United States Patent [19]
Yates

[11] Patent Number: 4,531,937
[45] Date of Patent: Jul. 30, 1985

[54] INTRODUCER CATHETER APPARATUS AND METHOD OF USE

[75] Inventor: Roy A. Yates, Los Angeles, Calif.

[73] Assignee: Pacesetter Systems, Inc., Sylmar, Calif.

[21] Appl. No.: 460,691

[22] Filed: Jan. 24, 1983

[51] Int. Cl.³ ............................................. A61M 5/00
[52] U.S. Cl. .................................... 604/53; 604/122; 604/164
[58] Field of Search .................................. 604/51–54, 604/158, 122, 164–169, 900

[56] References Cited

U.S. PATENT DOCUMENTS

| | | | |
|---|---|---|---|
| 3,399,674 | 9/1968 | Pannier et al. | 604/165 |
| 4,016,879 | 4/1977 | Mellor | 604/168 X |
| 4,217,895 | 8/1980 | Sagae et al. | 604/167 X |
| 4,311,137 | 1/1982 | Gerard | 604/167 X |

*Primary Examiner*—Dalton L. Truluck
*Attorney, Agent, or Firm*—Robert R. Meads; Bryant R. Gold

[57] ABSTRACT

The present invention is an introducer catheter apparatus having a body with a first bore along a longitudinal axis and a second bore in fluid communication with the first bore and extending from the first bore to the exterior surface at the side of the body, a fluid delivering means disposed on the second bore as the exterior surface of the body and the fluid communication with the second bore, and a flexible hollow tube means disposed in the first bore, a deformable sealing means disposed in the first bore between the second end of the body and the position within the first bore where the second bore connects to the first bore and a retractable needle means extends through the body including the deformable sealing means and a flexible hollow tube means and the tip of said needle when therein disposed extends past a distal end of the flexible hollow tube means.

20 Claims, 3 Drawing Figures

INTRODUCER CATHETER APPARATUS AND METHOD OF USE

DESCRIPTION

The technical field of the present invention is catheter apparatuses which are connected to human or animal users for use in delivery of drugs or other fluids either intravenously or subcutaneously.

BACKGROUND ART

In the past there have been problems associated with catheters used for delivery of fluids from drug delivery apparatuses. The problems were ones of maintaining the sterility of the catheter when being inserted in the human user and all necessary connections were being made to the drug delivery apparatus. There were also problems in effectively priming the conduit line from the drug delivery apparatus to the catheter and the catheter itself. Further, when there was a need for a prolonged period of drug delivery, the use of catheters was considered not feasible. With the introduction of flexible catheters there has been some renewed interests in their use for drug delivery systems but the other problems still existed.

Even though the advent of flexible catheters has provided an easy method for drug delivery, there was still a great deal of continued use of surgical insertions for human users who must use a drug delivery system over a long period of time. The continued use of surgical implantations was based primarily on the fact that it can be surgically implanted underneath the skin and the user would not have to worry particularly about it coming out.

The use of non-flexible and flexible catheters has always had the problem of unintentional removal by the human user due to some type of accident. Once this has taken place, then there is a continued problem of what to do to replace the catheter.

When there was a rigid tip catheter, it was very simple, catheter could be resterilized with a sterilizing fluid such as alcohol and it could then be reinserted intravenously or subcutaneously and fluid delivery could be continued as before. When flexible catheters were used, it was not as easy. Flexible catheters could not be reinserted because the flexible tip is blunt and cannot independently pierce the skin. Therefore, the catheter that had been removed from intervenous or subcutaneous insertion could not be reinserted. In such case, a new catheter has to be obtained and reinserted. It takes more than one person to carry out such catheter insertion and surely it would be difficult for a patient to carry these activities yet alone.

The prior art discloses flexible catheters. The Angiocath by Deseret is such a catheter and has a "Y" shape. The flexible catheter by Deseret has a retractable type needle within the confines of the flexible tip of the catheter which is used primarily for insertion into the human user. Once insertion is made the needle is removed and the delivery system is allowed to pump according to the delivery schedule for the individual user. However, there was quite a bit of problems with priming the system and determining when a vein has been properly pierced for fluid delivery to the human user.

In this type of catheter the hub of the needle has thereon disposed a porous end which will allow air to pass through but not liquid. Therefore, when a vein is pierced the blood will travel up the needle core to the hub. The air will be forced out of the porous needle hub but the blood will not pass through it. However, once the blood contacts the porous hub membrane, it clogs it and prevents it from further effective use. Therefore, if positioning was not precisely correct and it had to be repositioned it would be difficult to determine if position was correct because the system could not be purged and reused since the porous membrane was clogged.

In an attempt to make the process easier Deseret constructed a viewing chamber which is referred to as an "extension" which is used to view the blood after it passes through the needle core and into the hub prior to contacting the porous membrane. This attempts to provide an effective means to determine if the insertion is correct, but the same problems with the membrane existed. It could be clogged and rendered ineffective once contacted by blood. Additionally, this catheter had not solved the priming problem which existed for effectively and easily priming the catheter and line from the delivery apparatus.

Referring to the priming technique that existed for apparatuses as shown by Deseret, in order to properly prime the catheter, the needle tip of the flexible catheter must be inserted into the vein of the human user or subcutaneously. After the insertion, blood is allowed to back up through the core of the needle and allowed to trickle out of the back end of the needle hub indicating a proper intervenous insertion. Once this is carried out, there is priming of the system by retraction of the needle to the central body of the catheter to allow blood to back up through the Y section of the body to indicate that the catheter is primed with blood. Priming could not be carried out in body of the catheter with the fluid for the human user because like air in the body would be forced in the vein or subcutaneous insertion point of the flexible tip once the needle was removed to allow such priming.

This method is utilized by many. However, is very inefficient and there can be some sterility problems in carrying out the Priming method as described for prior art type flexible catheters. The sterility problems associated with priming are centered around opening the system to prime it and reconnecting the system. During these activities the system is susceptible to contact contamination.

Such contamination in some cases could cause infection, sickness or could even be fatal for the individual.

These and other problems are solved by the present invention.

DISCLOSURE OF INVENTION

The present invention is an introducer catheter apparatus.

The present invention is a flexible catheter which can be independently and easily primed while inserted in a human user. The catheter of the invention also has the ability to trap blood transmitted through the needle core in its hub to indicate that the catheter properly punctured a vein or improperly inserted subcutaneously, there is also an indicating means in the hub to indicate when proper priming of the catheter has taken place. The catheter can be inserted and primed in total sterility and therefore, not subject to contact contamination.

The catheter of the invention also is used in conjunction with a flow sensor or pressure indicating means which indicate internal conditions within the catheter. Such external devices are easily inserted within the catheter body and will provide independent indication of the above-described conditions within the catheter.

The catheter of the invention has a "Y" shape. It has a stepped longitudinal bore through the body. The longitudinal bore has connected thereto a drug delivery bore and a sensor bore. The catheter body has a flexible tubular tip attached to one end of the longitudinal bore. The catheter body and flexible tip have a hypodermic needle disposed therethrough for making the initial insertion in the human user. Once the needle is properly inserted and the system primed, the needle is removed and the flexible catheter delivers drugs and other fluids to the human user.

The hub of the needle has a hydrophilic material disposed therein for trapping blood and the priming fluid. This hydrophilic material is treated so that it will indicate when proper priming has taken place.

An object of the invention is to provide a catheter apparatus which can be primed while inserted in a human user in total sterility.

Another object of the invention is to provide a catheter apparatus which has priming indicating means and blood indicating means disposed in the hub of the hypodermic needle inserted through the catheter body.

A still further object of the invention is to provide a catheter with a means for inserting indicating means and/or flow indicating means within the catheter body.

These and other objects of the invention will be fully described in subsequent paragraphs.

BEST MODE FOR CARRYING OUT THE INVENTION

The present invention is an introducer catheter apparatus for the delivery of drugs to a human user.

Figure 1:
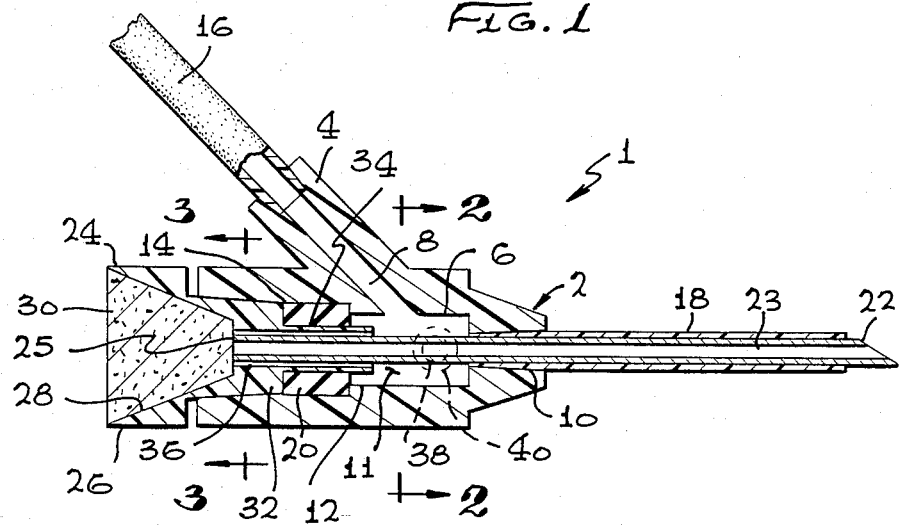
FIG. 1 shows a cut-away top view of the catheter of the invention.

FIG. 1 generally at 1, shows a top view of the apparatus of invention. The apparatus has a body 2 having a first central bore 6, a second bore 8 disposed through angularly outward extending arm 4 for receiving fluids from a delivery apparatus, and a third bore 38 for receiving therein pressure or flow sensing means for determining certain internal conditions within the catheter body. The central bore 6 has three stepped diameters along its length.

First stepped diameter bore section 10 of bore 6 is for fixably receiving flexible catheter tip 18. Flexible catheter tip 18 has an external diameter substantially the same as the interior diameter of the first stepped diameter bore section 10. Flexible tip 18 is constructed of a standard polyresin which has good memory after being flexed.

The second stepped diameter bore section 12 has connected thereto second bore 8, which receives the flow of drugs or other fluids from the delivery apparatus (not shown). Bore 8 is disposed in angularly outward extending arm 4. The outward extending arm 4 is disposed at an angle such that it forms a "Y" with the catheter body 2. The fluid to be delivered to the human user is delivered through flexible tube 16 to outward extending arm 4. Once delivered to outward extending arm 4, the fluid travels through a bore 8 to second stepped diameter section 12 of central bore 6.

Second stepped diameter bore section 12 of the central bore has a diameter greater than first stepped diameter bore section 10 such that there is an annular ledge formed between the first and second stepped bore sections. Therefore, there is chamber 11 formed in which fluid for delivery to the human user is stored prior to delivery to the human user.

Third stepped bore section 14 has a diameter greater than second stepped bore section 12. An annular ledge is formed at the junction of the second and third stepped bore sections. Third stepped bore section 14 is disposed such that it begins at a position in the central bore 6 past where the bores 8 and 38 enter the central bore 6.

Third stepped bore section 14 has therein disposed resealing rubber septum 20. Resealing septum 20 is disposed within the third stepped bore section such that the annular ledge between the second and third bore section acts as a shoulder stop for the septum. Septum 20 extends only part of the length of the third stepped bore section 14 and will act as a shoulder stop for the hypodermic needle hub, as will be described subsequently.

In the initial configuration, hypodermic needle 22, having hub 24, is inserted through the entire length of the catheter body and the flexible catheter tip 18. The needle and needle hub are retractable from the catheter body, once the catheter is in place and priming has taken place. The interaction of needle 22 and the catheter body 2 are important to the novelty of the invention.

Needle 22 is of a conventional type and has a central bore 23 that extends the length of the needle. Needle 22 has an outside diameter which is substantially the same as the inside diameter of flexible catheter tip 18. When needle 22 is disposed within the catheter body, it completely blocks fluid flow through flexible catheter tip 18 until the needle is retracted. Needle hub 24, which is fixably attached to needle 22 has three sections. First hub section 26 has a diameter greater than the diameter of third stepped bore section 14, such that it will not ingress that bore section. This hub acts as a stop means for ingress of the needle within catheter body 2. The first section also has a hollow portion 28, which also extends into second hub section 32. This hollow portion is filled with a hydrophilic material, which is used to absorb liquids in a procedure to be described subsequently.

Second hub section 32, which is connected to first section 26, has fixed therein end 25 of needle 22. As previously stated, hollow section 28 extends into second hub section 32. Needle 22 is disposed in second hub section 32 such that bore 23 is in fluid communication with hollow section 28. The second hub section 32 has a diameter substantially the same as third stepped bore section 14, so that, the second hub section 32 fits within third stepped bore section 14.

Third hub section 34 is connected to second hub section 32. Third hub section 34 has a diameter substantially less than the second hub section 32 such that an annular ledge is formed between the two hub sections. This annular ledge acts as a shoulder stop for the needle and hub when such annular ledge contacts the resealing rubber septum 20 disposed within third stepped section 14. The third hub section is hollow and has an outside diameter slightly larger than the diameter of needle 22. The inside diameter of third hub section 34 is substantially the same diameter as the outside diameter of needle 22 and needle 22 is disposed therethrough.

When the hub is fixed to end 25 of needle 22 and the assembly is disposed within catheter body 2, the third hub section extends through the resealing septum 20 and is disposed in chamber 11 of second stepped bore section 12 of central bore 6. The inside diameter of the second and third hub sections, which receive needle 22 therethrough, have a plurality aligned internal grooves 36. These grooves extend the length of the two hub sections. These grooves with the outside diameter of needle 22, when needle 22 is fixed therein, provide a plurality of fluid paths from the chamber 11 to the hollow section 28 in hub sections 26 and 32 containing hydrophilic material 30.

In operation, when the catheter generally shown 1 is to be inserted into an individual human user it is placed in either a vein or implanted subcutaneously. If the catheter is properly placed, blood will travel through central bore 23 of needle 22. This blood will be absorbed by the hydrophilic material 30 contained in hollow 28 of hub sections 26 and 32 while air is forced from the needle bore 23 passes through material 30 and expelled from the system. Visual sighting of the blood absorbed by the hydrophilic material will indicate that proper placement of the catheter tip has been realized.

Priming of the catheter is carried out while the catheter is inserted in the human user. During priming needle is fully inserted through catheter body 2 and flexible tip 18. To prime the catheter, fluid to be delivered to the human user is pumped through flexible line 16 through bore 8 into chamber 11 of second stepped bore section 12. As the fluid is pumped into second section 12 air and fluid will travel through grooves 36 in hub sections 32 and 34 to hollow 28. The air will pass through the hydrophilic material 30 and out of the system. The hydrophilic material may be treated with a material which will give an indication of the receipt by the material of such a fluid. This indication can be a change of color of the material or other common type of indication means to indicate proper priming of the chamber 11 in stepped section 12.

When both activities have taken place, (i.e., there is an indication of blood, indicating proper placement of the catheter tip, and an indication that the system is properly primed), needle 22 having hub 24 is removed from the catheter body. As they are withdrawn, resealing septum 20 will close behind the egress of needle 22 and seal section 14 of the central bore 6 from any egress of fluid from the chamber 11 of second stepped bore section 12. The fluid will then pass through from second stepped bore section 12 through the flexible tip 18. The flexible tip is not rigid and can sustain the activity of an individual without discomfort to the human user.

If at a later time it is determined that there is to be a change of fluid or other type of activity, needle 22 and its attached hub can be reinserted into the catheter body. During this reinsertion the needle is simply slipped through resealing septum 20 through chamber 11 of stepped bore section 12 and through the flexible tube 18. Once so inserted, the fluid flow is blocked through flexible tip 18. A new fluid source can be provided to bore 8 and the priming can take place, while the catheter is still in place, without the problem of blood drippage taking place. The system is primed as previously described, and all the old fluid is flushed from the chamber of second stepped section 12. Once this is done the needle is then removed and fluid is delivered to the human user as previously described.

Figure 2:
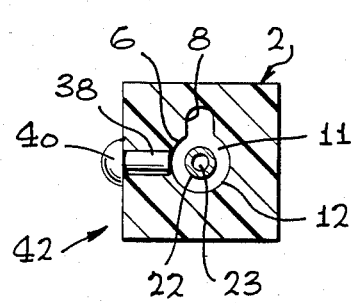
FIG. 2 shows a cross-sectional view of the catheter shown at 2—2 of FIG. 1.

Referring to FIG. 2, a cross-sectional view of the apparatus of the invention at 2—2 of FIG. 1 is shown generally at 42. Body 2 and the central bore 6 are shown. The portion of central bore 6 shown is chamber 11 of second stepped bore section 12. A portion of bore 8 is shown and its relationship with chamber 11. Also shown is an end view of a needle 22 showing the relationship of chamber 11. Disposed from the top of the apparatus is a bore 38 and disposed therein is plug 40.

When desired by the individual user a sensing apparatus, such as a flow sensor or pressure sensor, can be inserted within a bore 38. These are used to monitor the internal conditions of the interior catheter body. In situations where a flow sensor is connected to the apparatus through bore 38, the rate of flow through the catheter can be monitored to insure that there is no blockage taking place. In situations where a pressure sensor is disposed in bore 38, the pressure within the catheter can be monitored. Additionally the back pressure from heart activity can be monitored through the catheter body without any other external apparatuses being attached to the individual user.

Figure 3:
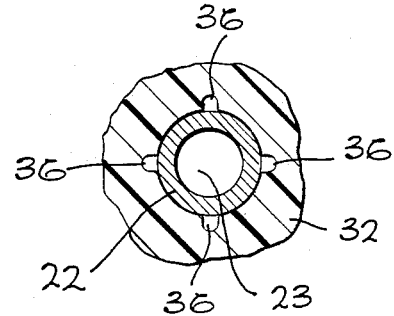
FIG. 3 shows a cross-sectional view of the catheter shown at 3—3 of FIG. 1.

Referring to FIG. 3, a cross-sectional view of the catheter is shown at 3—3 of FIG. 1. The second hub section 32 has a plurality of grooves 36 on its inside diameter. The outside surface of needle 22, which is fixed within the second and third hub sections, and the second and third hub section themselves with grooves 36 therein disposed, form fluid channels for fluid communication between chamber 11 and hydrophilic material 30 disposed in hollow section 22 in the first and second hub sections. This will allow for easy and bloodless priming of the catheter.

The terms and expressions which are employed here are used as terms of description and not of limitation and there is no indication, in the use of such terms and expressions, of expressing equivalence of the features shown, and described, or portions thereof, it being recognized that various modifications are possible in the scope of the invention as claimed.

I claim:

1. An introducer catheter apparatus comprising:
   (a) a body with a first bore along a longitudinal axis and a second bore connecting to and in fluid communication with the first bore and disposed from the first bore to an exterior side surface of the body;
   (b) a fluid transmitting means connected to the body and in fluid communication with the second bore;
   (c) a flexible hollow tube means fixed in the first bore at a first end of the body;
   (d) a deformable sealing means disposed in the first bore between a second opposite end of the body and the position within the first bore where the second bore connects to the first bore; and
   (e) a retractable needle means comprising a needle having a tip and an opposite end, and a hub affixed to such opposite end, the hub including fluid trapping means for trapping fluid therein and a first hub section extending along the needle toward the needle tip, the retractable needle means adapted to be disposed in an inserted position wherein the first hub section penetrates and extends through the deformable sealing means to the first bore and the needle extends through the deformable sealing means, the body and the flexible hollow tube means with the tip of said needle extending past a distal end of the flexible hollow tube means, the hub further including conduit means for providing fluid communication from the first bore to the fluid trapping means when the retractable needle means is in the inserted position.

2. The apparatus as recited in claim 1 wherein the junction of the first and second bore within the body form a "Y".

3. The apparatus as recited in claim 1 wherein the first bore has at least three steps in diametric size within said body.

4. The apparatus as recited in claim 3 wherein the first diametric step extends from the first end of the body to a point within the first bore to a forward point of the junction between the first and second bore, a second diametric step with a diameter greater than the first diametric step extends at least the length of the second bore opening within the first bore, a third diametric step within a diameter greater than the second diametric step extends from the second diametric step within the first bore to a second end of the body and an annular ledge is formed between said second and third diametric steps.

5. The apparatus as recited in claim 4 wherein the flexible tube means has an inside diameter substantially the same as the outside diameter of the needle, an outside diameter substantially the same as the diameter of the first diametric step, and when the needle is disposed through the flexible tube means fluid flow is blocked through the flexible tube means.

6. The apparatus as recited in claim 4 wherein the deformable sealing means is disposed in the third diametric step and the annular ledge formed between the second and third diametric steps acts as a shoulder stop for the deformable sealing means.

7. The apparatus as recited in claim 4 wherein the needle further comprises an elongated member having an outside diameter substantially the same as the diameter of the flexible tube means.

8. The apparatus as recited in claim 7 wherein the hub further comprises a second hub section of a size sufficient to prevent ingress of said second hub section into the first bore at the second end of the body and said second section having a hollow portion within which is retained the fluid trapping means, a third hub section with means connected to the second section having an outside diameter slightly less than the diameter of the third diametric step of the first bore in the body and a bore with an inside diameter substantially the same size as the outside diameter of the needle, and wherein the first hub section includes means connected to the third hub section having a diameter slightly larger than the outside diameter of the needle with a longitudinal bore of a diameter substantially the same as the outside diameter of the needle so the needle can be received therethrough, and wherein the conduit means comprises one or more grooves in fluid communication with the hollow portion, such grooves being formed into the third hub section bore and the first hub section longitudinal bore, such grooves and the outside diameter of the needle defining channels which provide fluid communication between the hollow portion of the second hub section and the first bore when the retractable needle means is in the inserted position.

9. The apparatus as recited in claim 8 wherein the fluid trapping means comprises a hydrophilic material disposed within the hollow in the first section of said hub.

10. The apparatus as recited in claim 1 wherein a third bore is disposed in said body in fluid communication with said first and second bores and extending from the first bore to an exterior side surface of the body.

11. The apparatus as recited in claim 10 wherein a detachable closure means is disposed in said third bore.

12. The apparatus as recited in claim 11 wherein the detachable closure means includes a plug to sterily seal the third bore in the body.

13. The apparatus as recited in claim 11 wherein the closure means includes a flow measuring means disposed in said third bore for measuring flow fluid within the catheter body.

14. The apparatus as recited in claim 11 wherein the closure means includes a pressure measuring means disposed in said third bore for measuring pressure within the catheter body.

15. A method of priming a catheter, said catheter including a body chamber, conduit means in fluid communication with said body chamber, and fluid trapping means in communication with said conduit means, said fluid trapping means including means for retaining a priming fluid therein without spillage, said method comprising the steps of:
(a) pumping the priming fluid into the catheter body chamber and replacing the air in the chamber with said fluid;
(b) expelling that air in said chamber through the conduit means and through the priming fluid trapping means; and
(c) transmitting at least a portion of said priming fluid through said conduit means when said chamber is substantially free of air and trapping said priming fluid in said trapping means without spillage indicating said catheter is primed.

16. The method as recited in claim 15 wherein the priming of the catheter is accomplished with said catheter being disposed in a user.

17. The method as recited in claim 15 wherein the priming of said catheter is accomplished with said catheter being free from connection to a user.

18. The method as recited in claim 15 wherein said trapping means includes indicating means disposed therein indicating when said catheter is primed.

19. The apparatus as recited in claim 1 wherein the needle has a central bore extending from the tip toward the opposite end and the fluid trapping means is also in fluid communication with such central bore, the fluid trapping means further including means for indicating the presence of priming fluid in the fluid trapping means.

20. An introducer catheter apparatus comprising:
(a) a body with a first bore along a longitudinal axis, a second bore connecting to and in fluid communication with the first bore and disposed from the first bore to an exterior side surface of the body;
(b) a fluid transmitting means connected to the body and in fluid communication with the second bore;
(c) a flexible hollow tube means fixed in the first bore at a first end of the body;
(d) a deformable sealing means disposed in the first bore between a second opposite end of the body and the position within the first bore where the second bore connects to the first bore; and
(e) a retractable needle means comprising a needle having a tip and a central bore extending from the tip toward an opposite end of the needle, and a hub affixed to such opposite end, the hub including fluid trapping means for trapping fluid therein and a hollow portion holding a hydrophilic material, the hydrophilic material being in fluid communication with the needle central bore and including means for indicating the presence of priming fluid in the fluid trapping means, and a hub section extending along the needle toward the needle tip, the retractable needle means adapted to be disposed in an inserted position wherein the hub section penetrates and extends through the deformable sealing means to the first bore and the needle extends through the deformable sealing means, the body and the flexible hollow tube means with the tip of the needle extending past a distal end of the flexible hollow tube means, the inside diameter of the flexible tube means being substantially the same as the outside diameter of the needle so as to prevent fluid flow therebetween, the hub section further including one or more conduits connecting the hydrophilic material and the first bore when the retractable needle means is in the inserted position.

* * * * *